United States Patent
Keppel

(10) Patent No.: US 7,044,948 B2
(45) Date of Patent: May 16, 2006

(54) CIRCUIT FOR CONTROLLING ARC ENERGY FROM AN ELECTROSURGICAL GENERATOR

(75) Inventor: David S. Keppel, Longmont, CO (US)

(73) Assignee: Sherwood Services AG, Schaffhausen (CH)

( * ) Notice: Subject to any disclaimer, the term of this patent is extended or adjusted under 35 U.S.C. 154(b) by 195 days.

(21) Appl. No.: 10/728,212

(22) Filed: Dec. 4, 2003

(65) Prior Publication Data

US 2004/0230189 A1 Nov. 18, 2004

Related U.S. Application Data

(60) Provisional application No. 60/432,384, filed on Dec. 10, 2002.

(51) Int. Cl.
*A61B 18/12* (2006.01)

(52) U.S. Cl. .................. 606/34; 606/606; 606/39; 606/40; 606/41; 606/49

(58) Field of Classification Search ............... 606/38, 606/40, 41, 46, 49, 34; 323/301, 911
See application file for complete search history.

(56) References Cited

U.S. PATENT DOCUMENTS

| | | |
|---|---|---|
| 1,787,709 A | 1/1931 | Wappler |
| 1,813,902 A | 7/1931 | Bovie |
| 1,841,968 A | 1/1932 | Lowry |
| 1,863,118 A | 6/1932 | Liebel |
| 1,945,867 A | 2/1934 | Rawls |
| 2,827,056 A | 3/1958 | Degelman |
| 2,849,611 A | 8/1958 | Adams |
| 2,982,881 A | 5/1961 | Reich |
| 3,058,470 A | 10/1962 | Seeliger et al. |
| 3,089,496 A | 5/1963 | Degelman |
| 3,163,165 A | 12/1964 | Islikawa |
| 3,252,052 A | 5/1966 | Nash |
| 3,391,351 A | 7/1968 | Trent |
| 3,402,326 A | 9/1968 | Guasco et al. |
| 3,413,480 A | 11/1968 | Biard et al. |
| 3,436,563 A | 4/1969 | Regitz |
| 3,439,253 A | 4/1969 | Piteo |
| 3,439,680 A | 4/1969 | Thomas, Jr. |
| 3,461,874 A | 8/1969 | Martinez |
| 3,471,770 A | 10/1969 | Haire |
| 3,478,744 A | 11/1969 | Leiter |
| 3,486,115 A | 12/1969 | Anderson |

(Continued)

FOREIGN PATENT DOCUMENTS

DE 179607 3/1905

(Continued)

OTHER PUBLICATIONS

Chicharo et al. "A Sliding Goertzel Algorith" Aug. 1996, pp. 283-297 Signal Processing, Elsevier Science Publishers B.V. Amsterdam, NL. vol. 52 No. 3.

(Continued)

*Primary Examiner*—Roy D. Gibson

(57) ABSTRACT

A circuit is disclosed which minimizes the amount of tissue vaporized during a first half (positive half cycle) of an electrosurgical current cycle and minimizes the amount of current applied to tissue during a second half (negative half cycle) of the electrosurgical current cycle to control thermal spread. The circuit is preferably provided within an electrosurgical generator which is capable of controlling the amount of energy delivered to a patient during electrosurgery on a per arc basis.

14 Claims, 2 Drawing Sheets

U.S. PATENT DOCUMENTS

| | | |
|---|---|---|
| 3,495,584 A | 2/1970 | Schwalm |
| 3,513,353 A | 5/1970 | Lansch |
| 3,514,689 A | 5/1970 | Giannamore |
| 3,515,943 A | 6/1970 | Warrington |
| 3,551,786 A | 12/1970 | Van Gulik |
| 3,562,623 A | 2/1971 | Farnsworth |
| 3,571,644 A | 3/1971 | Jakoubovitch |
| 3,589,363 A | 6/1971 | Banko |
| 3,595,221 A | 7/1971 | Blackett |
| 3,601,126 A | 8/1971 | Estes |
| 3,611,053 A | 10/1971 | Rowell |
| 3,641,422 A | 2/1972 | Farnsworth et al. |
| 3,662,151 A | 5/1972 | Haffey |
| 3,675,655 A | 7/1972 | Sittner |
| 3,683,923 A | 8/1972 | Anderson |
| 3,693,613 A | 9/1972 | Kelman |
| 3,697,808 A | 10/1972 | Lee |
| 3,699,967 A | 10/1972 | Anderson |
| 3,720,896 A | 3/1973 | Bierlein |
| 3,743,918 A | 7/1973 | Maitre |
| 3,766,434 A | 10/1973 | Sherman |
| 3,768,482 A | 10/1973 | Shaw |
| 3,783,340 A | 1/1974 | Becker |
| 3,784,842 A | 1/1974 | Kremer |
| 3,801,766 A | 4/1974 | Morrison, Jr. |
| 3,801,800 A | 4/1974 | Newton |
| 3,812,858 A | 5/1974 | Oringer |
| 3,815,015 A | 6/1974 | Swin et al. |
| 3,826,263 A | 7/1974 | Cage et al. |
| 3,828,768 A | 8/1974 | Douglas |
| 3,848,600 A | 11/1974 | Patrick, Jr. et al. |
| 3,870,047 A | 3/1975 | Gonser |
| 3,875,945 A | 4/1975 | Friedman |
| 3,885,569 A | 5/1975 | Judson |
| 3,897,787 A | 8/1975 | Ikuno et al. |
| 3,897,788 A | 8/1975 | Newton |
| 3,901,216 A | 8/1975 | Felger |
| 3,905,373 A | 9/1975 | Gonser |
| 3,913,583 A | 10/1975 | Bross |
| 3,923,063 A | 12/1975 | Andrews et al. |
| 3,933,157 A | 1/1976 | Bjurwill et al. |
| 3,946,738 A | 3/1976 | Newton et al. |
| 3,952,748 A | 4/1976 | Kaliher et al. |
| 3,963,030 A | 6/1976 | Newton |
| 3,964,487 A | 6/1976 | Judson |
| 3,971,365 A | 7/1976 | Smith |
| 3,980,085 A | 9/1976 | Ikuno |
| 4,005,714 A | 2/1977 | Hilebrandt |
| 4,024,467 A | 5/1977 | Andrews et al. |
| 4,041,952 A | 8/1977 | Morrison, Jr. et al. |
| 4,051,855 A | 10/1977 | Schneiderman |
| 4,063,557 A | 12/1977 | Wuchinich et al. |
| 4,074,719 A | 2/1978 | Semm |
| 4,092,986 A | 6/1978 | Schneiderman |
| 4,094,320 A | 6/1978 | Newton et al. |
| 4,102,341 A | 7/1978 | Ikuno et al. |
| 4,114,623 A | 9/1978 | Meinke et al. |
| 4,121,590 A | 10/1978 | Gonser |
| 4,123,673 A | 10/1978 | Gonser |
| 4,126,137 A | 11/1978 | Archibald |
| 4,145,636 A | 3/1979 | Doi |
| 4,188,927 A | 2/1980 | Harris |
| 4,191,188 A | 3/1980 | Belt et al. |
| 4,196,734 A | 4/1980 | Harris |
| 4,200,104 A | 4/1980 | Harris |
| 4,200,105 A | 4/1980 | Gosner |
| 4,209,018 A | 6/1980 | Meinke et al. |
| 4,231,372 A | 11/1980 | Newton |
| 4,232,676 A | 11/1980 | Herczog |
| 4,237,887 A | 12/1980 | Gosner |
| 4,237,891 A | 12/1980 | DuBose et al. |
| 4,281,373 A | 7/1981 | Mabille |
| 4,287,557 A | 9/1981 | Brehse |
| 4,303,073 A | 12/1981 | Archibald |
| 4,311,154 A | 1/1982 | Sterzer et al. |
| 4,314,559 A | 2/1982 | Allen |
| 4,321,926 A | 3/1982 | Roge |
| 4,334,539 A | 6/1982 | Childs et al. |
| 4,343,308 A | 8/1982 | Gross |
| 4,372,315 A | 2/1983 | Shapiro et al. |
| 4,376,263 A | 3/1983 | Pittroff et al. |
| 4,378,801 A | 4/1983 | Oosten |
| 4,384,582 A | 5/1983 | Watt |
| 4,397,314 A | 8/1983 | Vaguine |
| 4,407,272 A | 10/1983 | Yamaguchi |
| 4,411,266 A | 10/1983 | Cosman |
| 4,416,276 A | 11/1983 | Newton et al. |
| 4,416,277 A | 11/1983 | Newton et al. |
| 4,437,464 A | 3/1984 | Crow |
| 4,452,546 A | 6/1984 | Hiltebrandt et al. |
| 4,463,759 A | 8/1984 | Garito et al. |
| 4,470,414 A | 9/1984 | Imagawa et al. |
| 4,472,661 A | 9/1984 | Culver |
| 4,474,179 A | 10/1984 | Koch |
| 4,492,231 A | 1/1985 | Auth |
| 4,492,832 A | 1/1985 | Taylor |
| 4,494,541 A | 1/1985 | Archibald |
| 4,514,619 A | 4/1985 | Kugelman |
| 4,520,818 A | 6/1985 | Mickiewicz |
| 4,559,943 A | 12/1985 | Bowers |
| 4,565,200 A | 1/1986 | Cosman |
| 4,566,454 A | 1/1986 | Mehl et al. |
| 4,569,345 A | 2/1986 | Manes |
| 4,576,177 A | 3/1986 | Webster, Jr. |
| 4,582,057 A | 4/1986 | Auth et al. |
| 4,590,934 A | 5/1986 | Malis et al. |
| 4,608,977 A | 9/1986 | Brown |
| 4,630,218 A | 12/1986 | Hurley |
| 4,632,109 A | 12/1986 | Patterson |
| 4,644,955 A | 2/1987 | Mioduski |
| 4,646,222 A | 2/1987 | Okado et al. |
| 4,651,264 A | 3/1987 | Shiao-Chung Hu |
| 4,651,280 A | 3/1987 | Chang et al. |
| 4,657,015 A | 4/1987 | Irnich |
| 4,658,815 A | 4/1987 | Farin et al. |
| 4,658,819 A | 4/1987 | Harris et al. |
| 4,658,820 A | 4/1987 | Klicek |
| 4,662,383 A | 5/1987 | Sogawa et al. |
| 4,712,559 A | 12/1987 | Turner |
| 4,727,874 A | 3/1988 | Bowers et al. |
| 4,735,204 A | 4/1988 | Sussman et al. |
| 4,739,759 A | 4/1988 | Rexroth et al. |
| 4,741,334 A | 5/1988 | Irnich |
| 4,754,757 A | 7/1988 | Feucht |
| 4,805,621 A | 2/1989 | Heinze et al. |
| 4,818,954 A | 4/1989 | Flachenecker et al. |
| 4,827,911 A | 5/1989 | Broadwin et al. |
| 4,827,927 A | 5/1989 | Newton |
| 4,832,024 A | 5/1989 | Boussignac et al. |
| 4,848,335 A | 7/1989 | Manes |
| 4,848,355 A | 7/1989 | Nakamura et al. |
| 4,860,745 A | 8/1989 | Farin et al. |
| 4,862,889 A | 9/1989 | Feucht |
| 4,880,719 A | 11/1989 | Murofushi et al. |
| 4,890,610 A | 1/1990 | Kirwan et al. |
| 4,903,696 A | 2/1990 | Stasz et al. |
| 4,907,589 A | 3/1990 | Cosman |
| 4,922,210 A | 5/1990 | Flachenecker et al. |
| 4,931,047 A | 6/1990 | Broadwin et al. |
| 4,931,717 A | 6/1990 | Gray et al. |
| 4,938,761 A | 7/1990 | Ensslin |
| 4,942,313 A | 7/1990 | Kinzel |
| 4,961,047 A | 10/1990 | Carder |
| 4,961,435 A | 10/1990 | Kitagawa et al. |

| Patent | Type | Date | Inventor |
|---|---|---|---|
| 4,966,597 | A | 10/1990 | Cosman |
| RE33,420 | E | 11/1990 | Sussman |
| 4,969,885 | A | 11/1990 | Farin |
| 4,993,430 | A | 2/1991 | Shimoyama et al. |
| 4,995,877 | A | 2/1991 | Ams et al. |
| 5,015,227 | A | 5/1991 | Broadwin et al. |
| 5,019,176 | A | 5/1991 | Brandhorst, Jr. |
| 5,029,588 | A | 7/1991 | Yock et al. |
| 5,087,257 | A | 2/1992 | Farin |
| 5,103,804 | A | 4/1992 | Abele et al. |
| 5,108,389 | A | 4/1992 | Cosmescu |
| 5,108,391 | A | 4/1992 | Flachenecker |
| 5,122,137 | A | 6/1992 | Lennox |
| 5,133,711 | A | 7/1992 | Hagen |
| 5,151,102 | A | 9/1992 | Kamiyama et al. |
| 5,152,762 | A | 10/1992 | McElhenney |
| 5,157,603 | A | 10/1992 | Scheller et al. |
| 5,160,334 | A | 11/1992 | Billings et al. |
| 5,162,217 | A | 11/1992 | Hartman |
| 5,167,658 | A | 12/1992 | Ensslin |
| 5,190,517 | A | 3/1993 | Zieve et al. |
| 5,196,008 | A | 3/1993 | Kuenecke |
| 5,196,009 | A | 3/1993 | Kirwan, Jr. |
| 5,201,900 | A | 4/1993 | Nardella |
| 5,207,691 | A | 5/1993 | Nardella |
| 5,230,623 | A | 7/1993 | Guthrie et al. |
| 5,233,515 | A | 8/1993 | Cosman |
| 5,267,994 | A | 12/1993 | Gentelia et al. |
| 5,267,997 | A | 12/1993 | Farin |
| 5,281,213 | A | 1/1994 | Milder et al. |
| 5,300,068 | A | 4/1994 | Rosar et al. |
| 5,300,070 | A | 4/1994 | Gentelia |
| 5,318,563 | A | 6/1994 | Malis et al. |
| 5,323,778 | A | 6/1994 | Kandarpa et al. |
| 5,324,283 | A | 6/1994 | Heckele |
| 5,330,518 | A | 7/1994 | Neilson et al. |
| 5,334,193 | A | 8/1994 | Nardella |
| 5,341,807 | A | 8/1994 | Nardella |
| 5,342,356 | A | 8/1994 | Ellman |
| 5,342,357 | A | 8/1994 | Nardella |
| 5,342,409 | A | 8/1994 | Mullett |
| 5,348,554 | A | 9/1994 | Imran et al. |
| 5,370,645 | A | 12/1994 | Klicek et al. |
| 5,370,672 | A | 12/1994 | Fowler et al. |
| 5,370,675 | A | 12/1994 | Edwards et al. |
| 5,372,596 | A | 12/1994 | Klicek et al. |
| 5,383,874 | A | 1/1995 | Jackson |
| 5,383,876 | A | 1/1995 | Nardella |
| 5,383,917 | A | 1/1995 | Desai et al. |
| 5,385,148 | A | 1/1995 | Lesh et al. |
| 5,396,062 | A | 3/1995 | Eisentraut et al. |
| 5,400,267 | A | 3/1995 | Denen et al. |
| 5,403,311 | A | 4/1995 | Abele et al. |
| 5,403,312 | A | 4/1995 | Yates et al. |
| 5,409,000 | A | 4/1995 | Imran |
| 5,409,006 | A | 4/1995 | Buchholtz et al. |
| 5,409,485 | A | 4/1995 | Suda |
| 5,413,573 | A | 5/1995 | Koivukangas |
| 5,417,719 | A | 5/1995 | Hull et al. |
| 5,422,567 | A | 6/1995 | Matsunaga |
| 5,423,808 | A | 6/1995 | Edwards et al. |
| 5,423,809 | A | 6/1995 | Klicek |
| 5,423,810 | A | 6/1995 | Goble et al. |
| 5,430,434 | A | 7/1995 | Lederer et al. |
| 5,432,459 | A | 7/1995 | Thompson |
| 5,433,739 | A | 7/1995 | Sluijter et al. |
| 5,434,398 | A | 7/1995 | Goldberg |
| 5,436,566 | A | 7/1995 | Thompson |
| 5,438,302 | A | 8/1995 | Goble |
| 5,443,463 | A | 8/1995 | Stern et al. |
| 5,445,635 | A | 8/1995 | Denen |
| 5,451,224 | A | 9/1995 | Goble et al. |
| 5,458,597 | A | 10/1995 | Edwards et al. |
| 5,462,521 | A | 10/1995 | Brucker et al. |
| 5,472,441 | A | 12/1995 | Edwards et al. |
| 5,472,443 | A | 12/1995 | Cordis et al. |
| 5,478,303 | A | 12/1995 | Folry-Nolan et al. |
| 5,480,399 | A | 1/1996 | Hebborn |
| 5,483,952 | A | 1/1996 | Aranyi |
| 5,490,850 | A | 2/1996 | Ellman et al. |
| 5,496,312 | A | 3/1996 | Klicek |
| 5,496,313 | A | 3/1996 | Gentelia et al. |
| 5,500,012 | A | 3/1996 | Brucker et al. |
| 5,500,616 | A | 3/1996 | Ochi |
| 5,514,129 | A | 5/1996 | Smith |
| 5,520,684 | A | 5/1996 | Imran |
| 5,531,774 | A | 7/1996 | Schulman et al. |
| 5,534,018 | A | 7/1996 | Wahlstrand et al. |
| 5,536,267 | A | 7/1996 | Edwards et al. |
| 5,540,681 | A | 7/1996 | Strul et al. |
| 5,540,683 | A | 7/1996 | Ichikawa |
| 5,540,684 | A | 7/1996 | Hassler, Jr. |
| 5,540,724 | A | 7/1996 | Cox |
| 5,556,396 | A | 9/1996 | Cohen et al. |
| 5,558,671 | A | 9/1996 | Yates |
| 5,569,242 | A | 10/1996 | Lax et al. |
| 5,571,147 | A | 11/1996 | Sluijter et al. |
| 5,573,533 | A | 11/1996 | Strul |
| 5,588,432 | A | 12/1996 | Crowley |
| 5,594,636 | A | 1/1997 | Schauder |
| 5,596,466 | A | 1/1997 | Ochi |
| 5,599,344 | A | 2/1997 | Paterson |
| 5,599,345 | A | 2/1997 | Edwards et al. |
| 5,605,150 | A | 2/1997 | Radons et al. |
| 5,613,966 | A | 3/1997 | Makower et al. |
| 5,613,996 | A | 3/1997 | Lindsay |
| 5,625,370 | A | 4/1997 | D'Hont |
| 5,626,575 | A | 5/1997 | Crenner |
| 5,628,745 | A | 5/1997 | Bek |
| 5,643,330 | A | 7/1997 | Holsheimer et al. |
| 5,647,869 | A | 7/1997 | Goble et al. |
| 5,647,871 | A | 7/1997 | Levine et al. |
| 5,651,780 | A | 7/1997 | Jackson et al. |
| 5,658,322 | A | 8/1997 | Fleming |
| 5,660,567 | A | 8/1997 | Nierlich et al. |
| 5,688,267 | A | 11/1997 | Panescu et al. |
| 5,690,692 | A | 11/1997 | Fleming |
| 5,693,042 | A | 12/1997 | Bioarski et al. |
| 5,695,494 | A | 12/1997 | Becker |
| 5,702,386 | A | 12/1997 | Stern et al. |
| 5,702,429 | A | 12/1997 | King |
| 5,707,369 | A | 1/1998 | Vaitekunas et al. |
| 5,713,896 | A | 2/1998 | Nardella |
| 5,720,744 | A | 2/1998 | Eggleston et al. |
| 5,722,975 | A | 3/1998 | Edwards et al. |
| 5,733,281 | A | 3/1998 | Nardella |
| 5,749,869 | A | 5/1998 | Lindenmeier et al. |
| 5,749,871 | A | 5/1998 | Hood et al. |
| 5,755,715 | A | 5/1998 | Stern |
| 5,766,165 | A | 6/1998 | Gentelia et al. |
| 5,769,847 | A | 6/1998 | Panescu |
| 5,772,659 | A | 6/1998 | Becker et al. |
| 5,792,138 | A | 8/1998 | Shipp |
| 5,797,802 | A | 8/1998 | Nowak |
| 5,797,902 | A | 8/1998 | Netherly |
| 5,814,092 | A | 9/1998 | King |
| 5,817,093 | A | 10/1998 | Williamson, IV et al. |
| 5,820,568 | A | 10/1998 | Willis |
| 5,827,271 | A | 10/1998 | Bussey et al. |
| 5,830,212 | A | 11/1998 | Cartmell |
| 5,836,943 | A | 11/1998 | Miller, III |
| 5,836,990 | A | 11/1998 | Li |
| 5,846,236 | A | 12/1998 | Lindenmeier et al. |
| 5,868,737 | A | 2/1999 | Taylor et al. |
| 5,868,739 | A | 2/1999 | Lindenmeier et al. |
| 5,868,740 | A | 2/1999 | LeVeen et al. |

| | | | | | | |
|---|---|---|---|---|---|---|
| 5,871,481 | A | 2/1999 | Kannenberg et al. | 6,565,559 B1 | 5/2003 | Eggleston |
| 5,897,552 | A | 4/1999 | Edwards et al. | 6,573,248 B1 | 6/2003 | Ramasamy et al. |
| 5,908,444 | A | 6/1999 | Azure | 6,575,969 B1 | 6/2003 | Rittman, III et al. |
| 5,913,882 | A | 6/1999 | King | 6,620,157 B1 | 9/2003 | Dabney et al. |
| 5,921,982 | A | 7/1999 | Lesh et al. | 6,623,423 B1 | 9/2003 | Sakurai et al. |
| 5,925,070 | A | 7/1999 | King et al. | 6,635,057 B1 | 10/2003 | Harano |
| 5,931,836 | A | 8/1999 | Hatta et al. | 6,648,883 B1 | 11/2003 | Francischelli |
| 5,938,690 | A | 8/1999 | Law et al. | 6,652,514 B1 | 11/2003 | Ellman |
| 5,948,007 | A | 9/1999 | Starkenbaum et al. | 6,663,623 B1 | 12/2003 | Oyama et al. |
| 5,951,545 | A | 9/1999 | Schilling | 6,663,624 B1 | 12/2003 | Edwards |
| 5,951,546 | A | 9/1999 | Lorentzen | 6,666,860 B1 | 12/2003 | Takahashi |
| 5,954,686 | A | 9/1999 | Garito et al. | 6,679,875 B1 | 1/2004 | Honda |
| 5,954,717 | A | 9/1999 | Behl et al. | 6,682,527 B1 | 1/2004 | Strul |
| 5,971,980 | A | 10/1999 | Sherman | 6,685,700 B1 | 2/2004 | Behl |
| 5,976,128 | A | 11/1999 | Schilling et al. | 6,692,489 B1 | 2/2004 | Heim |
| 5,983,141 | A | 11/1999 | Sluijter et al. | 6,712,813 B1 | 3/2004 | Ellman |
| 6,010,499 | A | 1/2000 | Cobb | 6,730,080 B1 | 5/2004 | Harano |
| 6,014,581 | A | 1/2000 | Whayne et al. | 6,733,495 B1 | 5/2004 | Bek |
| 6,033,399 | A | 3/2000 | Gines | 6,733,498 B1 | 5/2004 | Paton |
| 6,044,283 | A | 3/2000 | Fein et al. | 6,740,079 B1 | 5/2004 | Eggers |
| 6,053,910 | A | 4/2000 | Fleenor | 6,740,085 B1 | 5/2004 | Hareyama |
| 6,053,912 | A | 4/2000 | Panescu et al. | 6,783,523 B1 | 8/2004 | Qin |
| 6,056,745 | A | 5/2000 | Panescu et al. | 6,790,206 B1 | 9/2004 | Panescu |
| 6,056,746 | A | 5/2000 | Goble et al. | 6,796,981 B1 | 9/2004 | Wham |
| 6,063,075 | A | 5/2000 | Mihori | 6,824,539 B1 | 11/2004 | Novak |
| 6,063,078 | A | 5/2000 | Wittkampf | 6,830,569 B1 | 12/2004 | Thompson |
| 6,068,627 | A | 5/2000 | Orszulak et al. | 6,843,789 B1 | 1/2005 | Goble |
| 6,074,386 | A | 6/2000 | Goble et al. | 6,849,073 B1 | 2/2005 | Hoey |
| 6,093,186 | A | 7/2000 | Goble | 6,855,141 B1 | 2/2005 | Lovewell |
| RE36,871 | E | 9/2000 | Epstein | 6,855,142 B1 | 2/2005 | Harano |
| 6,113,591 | A | 9/2000 | Whayne et al. | 6,860,881 B1 | 3/2005 | Sturm |
| 6,113,596 | A | 9/2000 | Hooven | 6,864,686 B1 | 3/2005 | Novak |
| 6,123,702 | A | 9/2000 | Swanson et al. | 6,875,210 B1 | 4/2005 | Refior |
| 6,132,429 | A | 10/2000 | Baker | 6,893,435 B1 | 5/2005 | Goble |
| 6,142,992 | A | 11/2000 | Cheng et al. | 2001/0031962 A1 | 10/2001 | Eggleston |
| 6,203,541 | B1 | 3/2001 | Keppel | 2002/0035353 A1 | 3/2002 | Edwards et al. |
| 6,210,403 | B1 | 4/2001 | Klicek | 2002/0035364 A1 | 3/2002 | Schoenman et al. |
| 6,228,080 | B1 | 5/2001 | Gines | 2002/0068932 A1 | 6/2002 | Edwards |
| 6,228,081 | B1 | 5/2001 | Goble | 2002/0193787 A1 | 12/2002 | Qin |
| 6,231,569 | B1 | 5/2001 | Bek | 2003/0060818 A1 | 3/2003 | Kannenberg |
| 6,235,020 | B1 | 5/2001 | Cheng et al. | 2003/0078572 A1 | 4/2003 | Pearson et al. |
| 6,238,387 | B1 | 5/2001 | Miller, III | 2003/0153908 A1 | 8/2003 | Goble |
| 6,238,388 | B1 | 5/2001 | Ellman | 2003/0163123 A1 | 8/2003 | Goble |
| 6,241,725 | B1 | 6/2001 | Cosman | 2003/0163124 A1 | 8/2003 | Goble |
| 6,245,065 | B1 | 6/2001 | Panescu | 2003/0171745 A1 | 9/2003 | Francischelli |
| 6,246,912 | B1 | 6/2001 | Sluijter et al. | 2003/0199863 A1 | 10/2003 | Swanson |
| 6,251,106 | B1 | 6/2001 | Becker et al. | 2004/0002745 A1 | 1/2004 | Flemming |
| 6,258,085 | B1 | 7/2001 | Eggleston | 2004/0019347 A1 | 1/2004 | Sakurai |
| 6,261,285 | B1 | 7/2001 | Novak | 2004/0024395 A1 | 2/2004 | Ellman |
| 6,273,886 | B1 | 8/2001 | Edwards | 2004/0030328 A1 | 2/2004 | Eggers |
| 6,275,786 | B1 | 8/2001 | Daners | 2004/0044339 A1 | 3/2004 | Beller |
| 6,293,941 | B1 | 9/2001 | Strul | 2004/0049179 A1 | 3/2004 | Francischelli |
| 6,306,131 | B1 | 10/2001 | Hareyama et al. | 2004/0054365 A1 | 3/2004 | Goble |
| 6,306,134 | B1 | 10/2001 | Goble et al. | 2004/0068304 A1 | 4/2004 | Paton |
| 6,309,386 | B1 | 10/2001 | Bek | 2004/0082946 A1 | 4/2004 | Malis |
| 6,337,998 | B1 | 1/2002 | Behl et al. | 2004/0097912 A1 | 5/2004 | Gonnering |
| 6,338,657 | B1 | 1/2002 | Harper et al. | 2004/0097914 A1 | 5/2004 | Pantera |
| 6,358,245 | B1 | 3/2002 | Edwards | 2004/0097915 A1 | 5/2004 | Refior |
| 6,383,183 | B1 | 5/2002 | Sekino et al. | 2004/0116919 A1 | 6/2004 | Heim |
| 6,398,779 | B1 | 6/2002 | Buysse et al. | 2004/0133189 A1 | 7/2004 | Sakurai |
| 6,398,781 | B1 | 6/2002 | Goble et al. | 2004/0138653 A1 | 7/2004 | Dabney |
| 6,402,741 | B1 | 6/2002 | Keppel et al. | 2004/0138654 A1 | 7/2004 | Goble |
| 6,402,743 | B1 | 6/2002 | Orszulak et al. | 2004/0172016 A1 | 9/2004 | Bek |
| 6,436,096 | B1 | 8/2002 | Hareyama | 2004/0230189 A1 | 11/2004 | Keppel |
| 6,451,015 | B1 | 9/2002 | Rittman, III et al. | 2004/0260279 A1 | 12/2004 | Goble |
| 6,458,121 | B1 | 10/2002 | Rosenstock | 2005/0004564 A1 | 1/2005 | Wham |
| 6,464,689 | B1 | 10/2002 | Qin | 2005/0021022 A1 | 1/2005 | Sturm et al. |
| 6,464,696 | B1 | 10/2002 | Oyama | 2005/0101951 A1 | 5/2005 | Wham |
| 6,506,189 | B1 | 1/2003 | Rittman, III et al. | 2005/0113818 A1 | 5/2005 | Sartor |
| 6,508,815 | B1 | 1/2003 | Strul | 2005/0113819 A1 | 5/2005 | Wham |
| 6,511,476 | B1 | 1/2003 | Hareyama | 2005/0149151 A1 | 7/2005 | Orszulak |
| 6,547,786 | B1 | 4/2003 | Goble | 2005/0182398 A1 | 8/2005 | Paterson |
| 6,562,037 | B1 | 5/2003 | Paton | | | |

| | | | |
|---|---|---|---|
| 2005/0197659 | A1 | 9/2005 | Bahney |
| 2005/0203504 | A1 | 9/2005 | Wham et al. |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 390937 | 4/1989 |
| DE | 3904558 | 8/1990 |
| DE | 3942998 | 7/1991 |
| DE | 19717411 A1 | 11/1998 |
| EP | 246350 | 11/1987 |
| EP | 310431 | 4/1989 |
| EP | 325456 | 7/1989 |
| EP | 336742 | 10/1989 |
| EP | 390937 | 10/1990 |
| EP | 556705 | 8/1993 |
| EP | 608609 | 8/1994 |
| EP | 836868 | 4/1998 |
| EP | 878169 | 11/1998 |
| EP | 1293171 | 3/2003 |
| FR | 1275415 | 10/1961 |
| FR | 1347865 | 11/1963 |
| FR | 2313708 | 12/1976 |
| FR | 2502935 | 10/1982 |
| FR | 2517953 | 6/1983 |
| FR | 2573301 | 5/1986 |
| GB | 855459 | 11/1960 |
| GB | 2164473 | 3/1986 |
| GB | 2214430 | 6/1989 |
| SU | 166452 | 1/1965 |
| SU | 727201 | 4/1980 |
| WO | WO92/06642 | 4/1992 |
| WO | WO93/24066 | 12/1993 |
| WO | WO94/24949 | 11/1994 |
| WO | WO94/28809 | 12/1994 |
| WO | WO95/09577 | 4/1995 |
| WO | WO95/19148 | 7/1995 |
| WO | WO96/02180 | 2/1996 |
| WO | WO 96/02180 | 2/1996 |
| WO | WO96/04860 | 2/1996 |
| WO | WO96/08794 | 3/1996 |
| WO | WO96/18349 | 6/1996 |
| WO | WO96/29946 | 10/1996 |
| WO | WO96/39914 | 12/1996 |
| WO | WO97/06739 | 2/1997 |
| WO | WO97/06740 | 2/1997 |
| WO | WO97/06855 | 2/1997 |
| WO | WO97/17029 | 5/1997 |
| WO | WO02/47565 | 6/2002 |
| WO | WO 03/092520 | 11/2003 |
| WO | WO 05/060365 | 11/2003 |

OTHER PUBLICATIONS

Ogden "Goertzel Alternative to the Fourier Transform" Jun. 1993 pp. 485-487 Electronics World; Reed Business Publishing, Sutton, Surrey, GB vol. 99, No. 1687.

International Search Report—PCT/US03/37310.

Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.

Anderson et al., "A Numerical Study of Rapid Heating for High Temperature Radio Frequency Hyperthermia" International Journal of Bio-Medical Computing, 35 (1994) pp. 297-307.

Astrahan, "A Localized Current Field Hyperthermia System for Use with 192-Iridium Interstitial Implants" Medical Physics, 9 (3), May/Jun. 1982.

Bergdahl et al., "Studies on Coagulation and the Development of an Automatic computerized Bipolar Coagulator" Journal of Neurosurgery 75:1, (Jul., 1991) pp. 148-151.

Cosman et al., "Methods of Making Nervous System Lesions" In William RH, Rengachary SS (eds): Neurosurgery, New York: McGraw-Hill, vol. 111, (1984), pp. 2490-2499.

Cosman et al., "Radiofrequency Lesion Generation and Its Effect on Tissue Impedance" Applied Neurophysiology 51: (1988) pp. 230-242.

Cosman et al., "Theoretical Aspects of Radiofrequency Lesions in the Dorsal Root Entry Zone" Neurosurgery 15:(1984) pp. 945-950.

Geddes et al., "The Measurement of Physiologic Events by Electrical Impedence" Am. J. MI, Jan. Mar. 1964, pp. 16-27.

Goldberg et al., "Tissue Ablation with Radiofrequency: Effect of Probe Size, Gauge, Duration, and Temperature on Lesion Volume" Acad Radio (1995) vol. 2, No. 5, pp. 399-404.

Medtrex Brochure "The O.R. Pro 300" 1 p.

Sugita et al., "Bipolar Coagulator with Automatic Thermocontrol" J. Neurosurg., vol. 41, Dec. 1944, pp. 777-779.

Valleylab Brochure "Valleylab Electroshield Monitoring System" 2 pp.

Vallfors et al., "Automatically Controlled Bipolar Electrosoagulation-'COA-COMP'" Neurosurgical Review 7:2-3 (1984) pp. 187-190.

Wald et al., "Accidental Burns", JAMA, Aug. 16, 1971, vol. 217, No. 7, pp. 916-921.

Richard Wolf Medical Instruments Corp. Brochure, "Kleppinger Bipolar Forceps & Bipolar Generator" 3 pp.

International Search Report—PCT/US03/37110.
International Search Report—PCT/US03/37310.
International Search Report—EP4009964.
International Search Report—EP98300964.8.
International Search Report—EP04015981.6.

Chicharo et al. "A Sliding Goertzel Algorith" Aug. 1996, pp. 283-297 Signal Processing, Elsevier Science Publishers B.V. Amsterdam, NL vol. 52 No. 3.

Ogden Goertzel Alternative to the Fourier Transform: Jun. 1993 pp. 485-487 Electronics World; Reed Business Publishing, Sutton, Surrey, BG vol. 99, No. 9. 1687.

CIRCUIT FOR CONTROLLING ARC ENERGY FROM AN ELECTROSURGICAL GENERATOR

CROSS REFERENCE TO RELATED APPLICATIONS

This application claims the benefit of priority to U.S. Provisional Application Ser. No. 60/432,384 filed on Dec. 10, 2002, the entire contents of which are hereby incorporated by reference herein.

BACKGROUND

1. Technical Field

The present disclosure is directed to electrosurgery and, in particular, to circuitry for controlling arc energy from an electrosurgical generator for ablating, cauterizing, coagulating, cutting and/or sealing body tissue during electrosurgery.

2. Description of the Related Art

Electrosurgical generators do not have the ability to vary the amount of energy contained within an arc to control the amount of tissue vaporized and the amount of current applied to tissue to limit collateral damage to surrounding tissue, e.g., thermal spread. The ultimate amount of arc energy from the electrosurgical generator to the tissue is dependent on patient resistance, power setting and the internal impedance of the electrosurgical generator.

Vaporization of tissue is proportional to the amount of energy in an arc. This energy in combination with the Cathode Fall Voltage, derives the power for vaporization. Thermal spread is dependent on the amount generated within the tissue is dependent on tissue resistive and the arc energy squared. As can be appreciated, by not controlling the thermal spread the depth of ablation is difficult to predict and control. Electrosurgery is thus disadvantageous in applications in which only a fine layer of tissue is to be ablated, or in areas of the body such as the heart or near the spinal cord where resistive heating can result in undesirable collateral damage to critical tissue and/or organs.

U.S. Pat. No. 6,413,256 B1 to Truckai et al. discloses an electrosurgical system where a spark gap is utilized in series with the electrosurgical generator output current to control resistive heating of tissue during electrosurgery. The spark gap limits the arc energy, but is prone to introducing high frequency oscillations that can have an undesirable effect on the tissue, as well as increase the high frequency leakage currents.

Therefore, it is an aspect of the present disclosure to provide a circuit for controlling arc energy from the electrosurgical generator to minimize the amount of tissue vaporized and to also minimize the amount of current applied to tissue to limit thermal spread without introducing high frequency oscillations or other undesirable effects.

SUMMARY

A circuit is disclosed which minimizes the amount of tissue vaporized during a first half (positive half cycle) of an electrosurgical current cycle and minimizes the amount of current applied to tissue during a second half (negative half cycle) of the electrosurgical current cycle to limit thermal spread. The circuit is preferably provided within an electrosurgical generator to provide an electrosurgical generator which is capable of controlling the amount of energy delivered to a patient during electrosurgery on a per arc basis.

In a first embodiment, the circuit includes a diode-resistor block having a pair of diodes in series with an output current of the electrosurgical generator. In a second embodiment, the diode-resistor block includes the pair of diodes in parallel with the output current of the electrosurgical generator. In both embodiments, each diode is biased opposite from the other diode, thus splitting the output current into two paths. The diode-resistor block in both embodiments includes two resistors which are provided in each of the two paths. These resistors, depending on their resistive value, limit the current for each half cycle.

As long as the current for either half cycle remains above a predetermined minimum current, $I_{min}$, an arc is formed. The energy in the arc is limited by the resistors. Accordingly, the arc energy for vaporizing tissue during the positive half cycle and the arc energy for causing thermal spread during the negative half cycle are controlled.

In alternate embodiments, the resistors of the diode-resistor block are replaced with potentiometers for allowing a user of the electrosurgical generator to "dial" in preferred levels of tissue vaporization and thermal spread. With these embodiments, the surgeon is given an almost unlimited ability to vary the ratio between the amount of tissue vaporized and thermal spread.

Further features of the above embodiments will become more readily apparent to those skilled in the art from the following detailed description of the apparatus taken in conjunction with the drawings.

BRIEF DESCRIPTION OF THE DRAWINGS

Various embodiments will be described herein below with reference to the drawings wherein.

DETAILED DESCRIPTION

Figure 1:
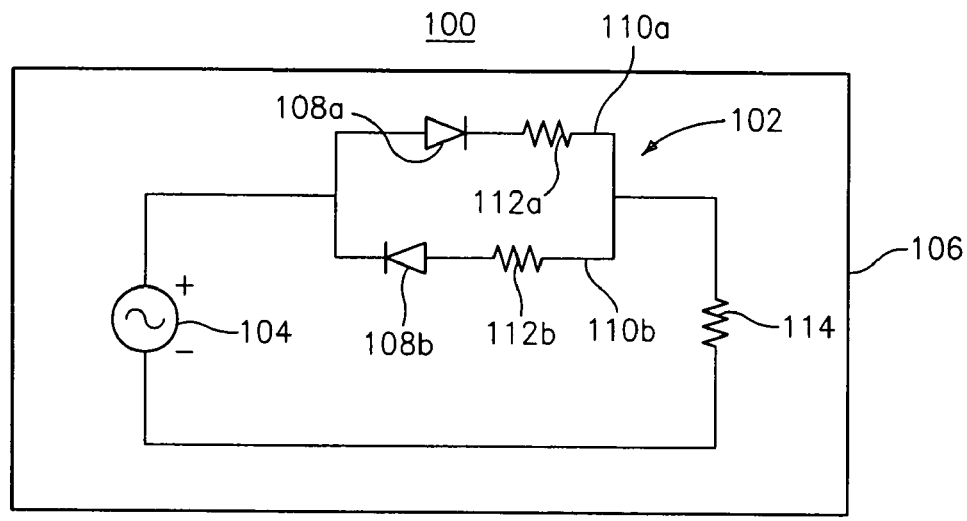
FIG. 1 is a schematic diagram of a circuit according to a first embodiment.

Reference is made to the drawings where like reference numerals refer to similar elements. Referring to FIG. 1, there is shown a schematic diagram of a circuit according to one embodiment of the present disclosure generally identified by reference numeral 100. Circuit 100 includes a diode-resistor block 102 in series with an output current 104 of an electrosurgical generator 106. The diode-resistor block 102 includes a pair of diodes 108a, 108b biased opposite from each other, thus splitting the output current 104 into two paths 110a, 110b. Preferably, the diodes 108a and 108b are high voltage, fast recovering diodes.

The diode-resistor block 102 further includes resistors 112a, 112b in each of these two paths 110a, 110b. These resistors 112a, 112b, depending on their resistive value (including having no resistive value, i.e., short), limit the current for each half cycle of the output current 104. Preferably, the resistance value for resistors 112a and 112b is in the range of about 50 ohms to about 2000 ohms.

The output current 104 is further limited by the patient resistance 114 in series with the diode-resistor block 102. The resistive value of the resistor 114 is typically in the range of 100 to 4000 ohms. By limiting the current for the positive half cycle, the circuit 100 controls the amount of vaporization of the tissue. By limiting the current for the negative half cycle, the circuit 100 controls thermal spread to surrounding tissue. During the periods of reduced power, the thermal energy is allowed to dissipate which reduces the overall thermal conduction and reduces the amount of steam exiting the surgical site. A detailed explanation of this effect is disclosed in commonly-assigned U.S. Pat. No. 6,228,080, the entire contents of which are hereby incorporated by reference herein.

In circuit 100, the voltage can drop at two spots: across resistor 112a and across patient 114 for maintaining arc at a predetermined minimum voltage, $V_{min}$, the minimum voltage point at which the arc disappears). As can be appreciated, as long as the current for either half cycle remains above a predetermined minimum current, $I_{min}$, an arc is formed. The energy in the arc is limited by the resistors 112a and 112b and patient resistance 114. Accordingly, the arc energy for vaporizing tissue during the positive half cycle and the arc energy for causing thermal spread during the negative half cycle are controlled.

It is provided that according to the resistive values selected for the resistors 112a and 112b the output current 104 may be limited for only one of the half cycles.

Figure 3:
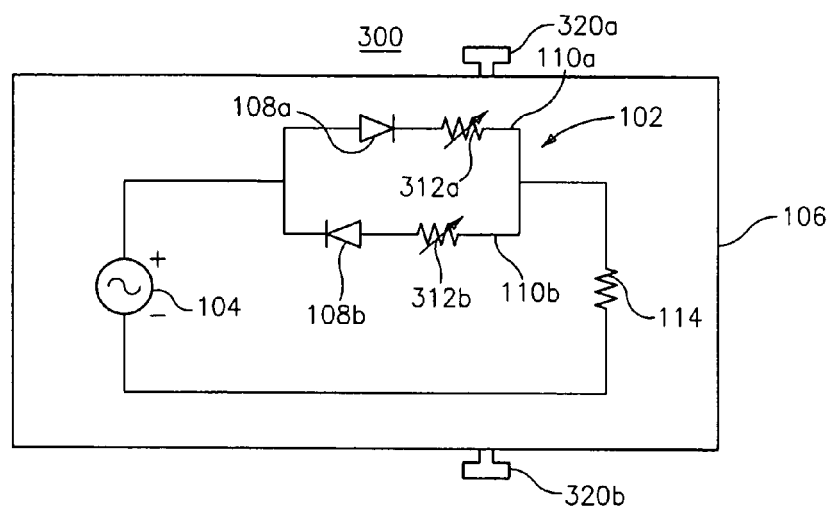
FIG. 3 is a schematic diagram of a circuit according to a third embodiment.

In an alternate embodiment according to the present disclosure as shown by FIG. 3, a circuit 300 is provided which is similar to circuit 100. However, in this embodiment, the resistors 112a, 112b are replaced with potentiometers 312a, 312b for allowing a surgeon to select the resistive value (including no resistive value, i.e., short) for potentiometers 312a, 312b using dials 320a, 320b, respectively, on the electrosurgical generator 106 for varying the ratio between the amount of tissue vaporized during the positive half cycle and thermal spread during the negative half cycle. In circuit 300, the voltage can drop at two spots: across potentiometer 312a and across the patient 114 for maintaining arc at a predetermined minimum voltage, $V_{min}$.

It is envisioned that by selecting the resistive values for the potentiometers 312a and 312b, the output current 104 may be limited for only one of the half cycles.

Figure 2:
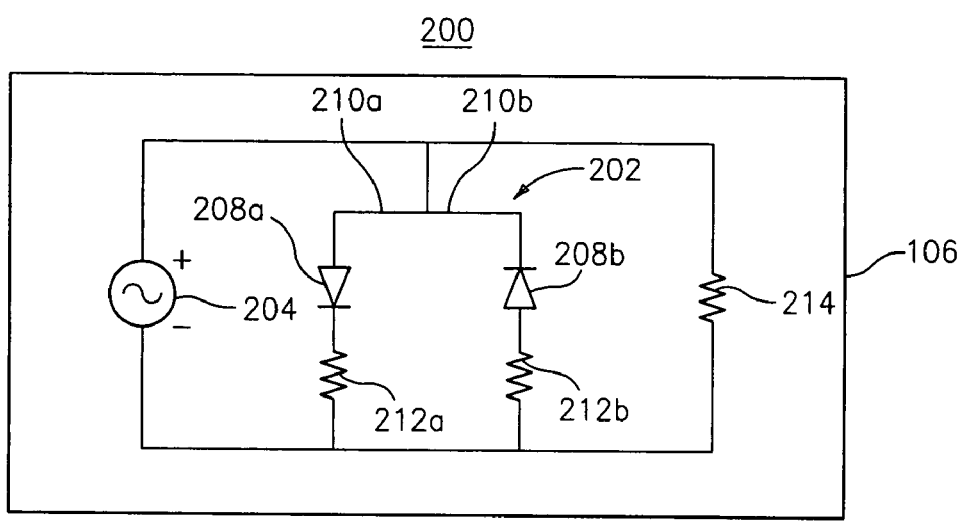
FIG. 2 is a schematic diagram of a circuit according to a second embodiment.

Referring to FIG. 2, there is shown a schematic diagram of a circuit 200 according to another embodiment of the present disclosure. Circuit 200 includes a diode-resistor block 202 in parallel with the output current 204 of an electrosurgical generator 206. The diode-resistor block 202 includes a pair of diodes 208a, 208b biased opposite from each other, thus splitting the output current 204 into two paths 210a, 210b. The diode-resistor block 202 shunts the current around the patient 214. This forms two paths; the path through the diode circuit block 202 and the path through the patient 214.

The diode-resistor block 202 further includes resistors 212a, 212b in each of these two paths 210a, 210b, respectively. These resistors 212a, 212b, depending on their resistive value (including having no resistive value, i.e., short), shunt the current for each half cycle of the output current 204.

The output current 204 is further limited by the patient resistance 214 in parallel with the diode-resistor block 202. The resistive value of the patient 214 is typically in the range of 100 to 4000 ohms. By shunting the current for the positive half cycle, the circuit 200 controls the amount of vaporization of the tissue. By shunting the current for the negative half cycle, the circuit 200 controls thermal spread to surrounding tissue. In circuit 200, the predetermined minimum voltage, $V_{min}$, is controlled within the generator 106 and, thus, the voltage does not drop across the patient 214 to maintain or control $V_{min}$.

In short, as long as the current for either half cycle remains above a predetermined minimum current, $I_{min}$, an arc is formed. The energy in the arc is shunted by the resistors 212a and 212b. Accordingly, the arc energy for vaporizing tissue during the positive half cycle and the arc energy for causing thermal spread during the negative half cycle are adequately controlled. Moreover and depending upon the resistive values selected for the resistors 212a and 212b the output current 204 may be limited for only one of the half cycles.

Figure 4:
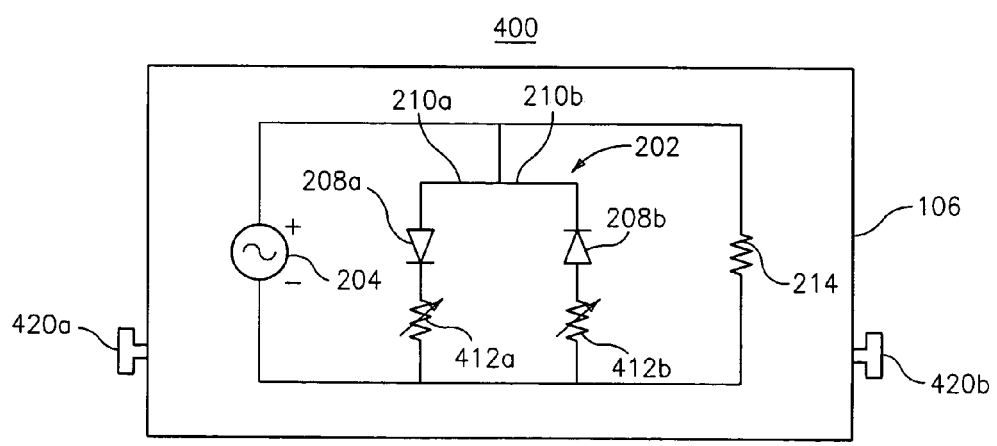
FIG. 4 is a schematic diagram of a circuit according to a fourth embodiment.

In an alternate embodiment, as shown by FIG. 4, a circuit 400 is provided which is similar to circuit 200. However, in this embodiment, the resistors 212a, 212b are replaced with potentiometers 412a, 412b for allowing a surgeon to select the resistive value (including no resistive value, i.e., short) for potentiometers 412a, 412b using dials 420a, 420b, respectively, on the electrosurgical generator 106 for varying the ratio between the amount of tissue vaporized during the positive half cycle and thermal spread during the negative half cycle. Much like circuit 200 described above, in 400 the predetermined minimum voltage, $V_{min}$, is controlled within the generator 106 and thus, the voltage does not drop across the patient 214 to maintain or control $V_{min}$. The output current 104 may be shunted for only one of the half cycles by selecting the values for the potentiometers 412a and 412b.

Accordingly, the present disclosure provides an electrosurgical generator which is capable of controlling the amount of energy delivered to a patient during electrosurgery on a per arc basis. As can be appreciated, controlling the power reduces the overall effect on the tissue and the surrounding tissue.

Although the present disclosure has been described with respect to preferred embodiments, it will be readily apparent to those having ordinary skill in the art to which it appertains that changes and modifications may be made thereto without departing from the spirit or scope of the disclosure.

What is claimed is:

1. A circuit for controlling arc energy from an electrosurgical generator, said circuit comprising:
    means for receiving an output current generated by the electrosurgical generator; and
    a diode-resistor block electrically connected to said means for receiving the output current, said diode-resistor block configured to limit the amount of output current for at least one half cycle of the output current; said diode-resistor block including a pair of diodes biased opposite from each other and configured to split the output current into two paths, each of the two paths including one of a resistor and a potentiometer in series with a respective diode of the pair of diodes.

2. A current according to claim 1, wherein said diode-resistor block is connected in series to said means for receiving the output current.

3. A circuit according to claim 1, wherein said diode-resistor block is connected in parallel with said means for receiving the output current.

4. A circuit according to claim 1, further comprising a resistor in series with said diode-resistor block.

5. A circuit according to claim 1, further comprising a resistor in parallel with said diode-resistor block.

6. An electrosurgical generator for controlling the amount of energy delivered to a patient during electrosurgery on a per arc basis, the electrosurgical generator comprising:
    a circuit including:
        means for receiving an output current generated by the electrosurgical generator; and means for limiting the amount of output current for at least one half cycle of the output current; said means for limiting the amount of output current for at least one half cycle of the output current including a pair of diodes biased opposite from each other for splitting the output current into two paths, each of the two paths including one of a resistor and a potentiometer in series with a respective diode of the pair of diodes.

7. An electrosurgical generator according to claim 6, wherein said means for limiting the amount of output current for at least one half cycle of the output current includes a diode-resistor block in series with said means for receiving the output current.

8. An electrosurgical generator according to claim 6, wherein said means for limiting the amount of output current for at least one half cycle of the output current includes a diode-resistor block in parallel with said means for receiving the output current.

9. An electrosurgical generator according to claim 6, further comprising a resistor in series with said means for limiting the amount of output current for at least one half cycle of the output current.

10. An electrosurgical generator according to claim 6, further comprising a resistor in parallel with said means for limiting the amount of output current for at least one half cycle of the output current.

11. A method for controlling arc energy from an electrosurgical generator, said method comprising the steps of:

receiving an output current generated by the electrosurgical generator; and limiting the amount of output current for at least one half cycle of the output current by splitting the output current into two paths using a pair of diodes biased opposite from each other and providing in each of the two paths one of a resistor and a potentiometer in series with a respective diode of the pair of diodes.

12. A method according to claim 11, wherein said step for limiting the amount of output current for at least one half cycle of the output current comprises the step of providing a diode-resistor block in series with the output current.

13. A method according to claim 11, wherein said step for limiting the amount of output current for at least one half cycle of the output current comprises the step of providing a diode-resistor block in parallel with the output current.

14. A method according to claim 11, further comprising the step of varying the resistive value for one of the resistor and the potentiometer.

* * * * *